United States Patent
Li et al.

(10) Patent No.: US 6,463,411 B1
(45) Date of Patent: Oct. 8, 2002

(54) SYSTEM AND METHOD FOR PROCESSING LOW SIGNAL-TO-NOISE RATIO SIGNALS

(76) Inventors: Xinde Li, 8 Lomond Drive, Apt. 2003, Toronto, Ontario (CA), M8X 2W3; Yuri Sokolov, 2429 Cliff Road, Mississauga Ontario (CA), L5A 2P1; Hans Kunov, 4 Princeton Road, Etobicoke, Ontario (CA), M8X 2E2

(*) Notice: Subject to any disclaimer, the term of this patent is extended or adjusted under 35 U.S.C. 154(b) by 0 days.

(21) Appl. No.: 09/849,451

(22) Filed: May 7, 2001

Related U.S. Application Data

(63) Continuation of application No. PCT/CA99/01055, filed on Nov. 8, 1999.
(60) Provisional application No. 60/107,571, filed on Nov. 9, 1998.

(51) Int. Cl.[7] ............... H04B 15/00; G10L 21/02; H04R 25/00
(52) U.S. Cl. ............... 704/226; 381/71.6; 381/317
(58) Field of Search ................ 704/226, 227, 704/228; 381/71.6, 71.11, 71.14, 312, 317; 600/559

(56) References Cited

U.S. PATENT DOCUMENTS

| | | | | |
|---|---|---|---|---|
| 3,984,634 A | * | 10/1976 | Painter | 375/348 |
| 4,989,170 A | * | 1/1991 | Batruni et al. | 375/231 |
| 5,165,051 A | * | 11/1992 | Kumar | 324/76.39 |
| 5,413,114 A | * | 5/1995 | Zurek et al. | 600/559 |
| 5,615,208 A | * | 3/1997 | Hagmanns | 370/252 |
| 5,867,411 A | * | 2/1999 | Kumar | 375/232 |
| 5,943,429 A | * | 8/1999 | Handel | 381/94.2 |

* cited by examiner

Primary Examiner—Marsha D. Banks-Harold
Assistant Examiner—Martin Lerner
(74) Attorney, Agent, or Firm—Kevin Pillay; Fasken Martineau DuMoulin LLP

(57) ABSTRACT

A system and method for use in a real time system and for processing a signal with a low signal-to-noise ratio (SNR). The system comprises a model for modeling an expected signal and a filter that uses the model for filtering the signal. The filter is used for generating a prediction of the signal and an error variance matrix. The system further comprises an adaptive element for modifying the error variance matrix such that the bandwidth of the filter is widened, wherein the filter behaves like an adaptive filter.

28 Claims, 6 Drawing Sheets

SYSTEM AND METHOD FOR PROCESSING LOW SIGNAL-TO-NOISE RATIO SIGNALS

This application is a continuation of application Ser. No. PCT/CA 99/01055, filed Nov. 8, 1999, which claims benefit of Provisional application Ser. No. 60/107,571, filed Nov. 9, 1998.

The present invention relates generally to a system and method for processing signals with low signal-to-noise ratios (SNRs), and particularly to physiological signals with low SNRS.

BACKGROUND OF THE INVENTION

In certain applications it is necessary to analyze physiological signals which are contaminated with noise. These signals often have low amplitudes, which results in a poor signal-to-noise ratio (SNR). A poor SNR causes difficulty in signal processing and requires complex, lengthy algorithms for processing the signals with accuracy. In some cases, not only does the physiological signal occur with poor SNRs, but also the stimuli that elicit such a physiological signal are of the same mode, or nature, as the signal. Such stimuli can affect the data acquisition process or contaminate the signal.

Such a problem is demonstrated in current methods used to test an individual's hearing. It is known that the introduction to the ear canal of an acoustic stimulus results in the production of numerous audible intermodulation distortion products. The acoustic stimulus comprises two single frequency sinusoidal tones, called primaries, at frequencies $f_1$ and $f_2$ with the levels of about 30 to 75 dB Sound Pressure Level (SPL). A normal inner ear will then produce sinusoidal mechanical responses at additional frequencies, the stronger component of which occurs at frequency $2f_1-f_2$ (the cubic Distortion Product Otoacoustic Emission, DPOAE). This energy is transferred by the middle ear back into the ear canal where it appears as an acoustic signal. The origin of DPOAE lies in the mechanical non-linearity of the cochlea due to internal active processes, associated with the motility of the outer hair cells. The phenomenon is intrinsic to the normally functioning inner ear. Thus, the presence or absence of DPOAE provides strong evidence of inner ear function (or dysfunction), making it a valuable diagnostic and screening tool.

However, detection of a DPOAE signal is difficult because its level is very low (that is the sound is very soft). and is typically between minus 15 and plus 10 dB SPL. As a consequence of background physiological, acoustic, and instrumentation noise, which is typically about 30 to 50 dB SPL, the signal-to-noise ratio is very poor.

Several solutions have been proposed thus far, two of which are described in U.S. Pat. No. 5,413,114 (which is a divisional of U.S. Pat. No. 5,267,571) and U.S. Pat. No. 5,664,577 (which is a continuation of U.S. Pat. No. 5,526, 819). The contents of these references are incorporated herein by reference. U.S. Pat. No. 5,413,114 teaches a system and method for testing hearing by presenting multiple single frequency tones to an individual. The multiple frequencies are used for preventing numerous intermodulation products. However, the invention does not provide any way of reducing other noise influences. The signal-to-noise ratio, while improved, is still low and therefore many of the problems remain unchanged. U.S. Pat. No. 5,664,577 teaches a system and a method for reducing the noise levels in the system by collecting multiple readings for the intermodulation products and taking the average value. Also, two microphones are used with a differential amplifier for reducing the noise.

These and other solutions are plagued by many technical and clinical disadvantages. At present, most instruments for detection of signals in noise use signal processing methods which employ averaging in the time domain and Fast Fourier Transforms (FFT).

Because of the need to average several time segments in these methods, there is a time delay before the signal is known. This delay is even larger in the presence of artifacts. In the case of DPOAE artifacts can arise from irregular breathing, patient or operator movements, and environmental noise such as shutting of doors, sounds of equipment, steps of personnel and the like. Further, the averaged time signal contains artifacts due to the time segmentation. These artifacts are to be rejected from averaging, and therefore increase the delay. Also, the FFT data does not allow the signal to be monitored and output (or played back) in real time.

The aforementioned technical factors cause clinical disadvantages, which decrease the clinical value of the present-day methods. Because the signal can not be directly output, for example, DPOAEs cannot be output to a speaker. Therefore, they cannot be detected and/or monitored by an operator. Because the signal can not be quickly analyzed when the frequencies of stimuli are varying in time, it is very time consuming to obtain a frequency response of the signal, that is, its amplitude as a monotonous function of the stimulus frequency. This can be important, for example, for DPOAEs because their amplitude varies significantly with very little change in the frequencies of primary tones.

The use of averaging techniques allows the clinician to obtain the signals only at certain times, and does not allow him/her to continually monitor the signal's level in time. In certain situations, this is critical. For example, during an operation on the acoustic nerve, DPOAE level can indicate the physiological state of the cochlea and help prevent a cochlear catastrophe caused by interruption of blood supply. Another example is in titrating ototoxic drugs, DPOAE level monitoring can help prevent drug-induced cochlear injury.

Another example of physiological signal significantly contaminated by noise is Auditory Steady State Response (ASSR). ASSR is an electric sinusoidal signal, supposedly originating in the brainstem, elicited by a modulated sinusoidal stimulus. The stimulus is typically a carrier tone of audible frequency range the amplitude or frequency of which is modulated with low modulation frequency typically between 40 and 100 Hz. The ASSR signal has exactly the frequency of such modulation, and very low amplitude, which causes difficulty for reliably extracting it from noise.

The principle of ASSR measurement is described as follows. A modulated pure tone is presented to the ear. The carrier frequencies are usually conventional audiometric tones, from 125 to 8000 Hz. The levels of the frequencies are at or higher than 20 dB SPL. The modulation frequencies are typically 40 Hz or within the 70 to 100 Hz range (usually 80 Hz if they are in the 70 to 100 Hz range), with a 0.95 modulation index.

At the time of stimulation, a sinusoidal electric signal, which has the frequency equal to the modulation frequency of the stimulus, appears on the surface of the skull. This signal, supposedly produced by the brainstem, is called the ASSR. The ASSR can be recorded from the surface of the skull with three electrodes, typically on the vertex, on the temporal bone, and on the lobule. This electric signal, whose magnitude is typically from 40 to 400 nV, is then amplified with a typical gain of approximately 10,000 V/V. It is then passed through a band pass filter, with a typical lower frequency cutoff at 10 to 30 Hz and a higher frequency cutoff at 100 to 300 Hz. It is converted into its digital form and processed.

Techniques for ASSR detection suffer from the same drawbacks as those for DPOAE; however, a particular disadvantage of ASSRs is that their detection with current signal processing techniques requires long recording times.

It is an object of the present invention to obviate or mitigate at least some of the disadvantages discussed above.

SUMMARY OF THE INVENTION

The present invention provides a system for use in a real time system and for processing a signal with a low signal-to-noise ratio (SNR). The system comprises a model for modeling an expected signal and a filter that uses the model for filtering the signal. The filter is used for generating a prediction of the signal and an error variance matrix. The system further comprises an adaptive element for modifying the error variance matrix such that the bandwidth of the filter is widened, wherein the filter behaves like an adaptive filter.

The present invention further provides a system for processing a signal with a low signal-to-noise ratio (SNR) for providing output to an operator. The system comprises a model for modeling an expected signal, a filter using the model for filtering the signal for generating a prediction of the signal and an error variance matrix. The system further comprises an adaptive element for modifying the error variance matrix such that the bandwidth of the filter is widened. A processor is provided for processing the filtered signal for determining its signal characteristics, and an output is used for providing the signal characteristics to the operator. The system provides the output to the operator in real-time.

The present invention further provides a method for use in a real time system and for processing a signal with a low signal-to-noise ratio (SNR). The method comprises the steps of modeling an expected signal, filtering the signal for generating a signal prediction and an error variance matrix, modifying said error variance matrix such that the bandwidth is widened, processing the filtered signal for determining the signal characteristics, and providing the signal characteristics to an operator. The method provides said output to the operator in real-time.

BRIEF DESCRIPTION OF THE DRAWINGS

The invention will now be described by way of example with reference to the following drawings in which.

DETAILED DESCRIPTION OF THE PREFERRED EMBODIMENT

According to an embodiment of the invention, a method employs a linear minimum mean-square error filter, know as the Kalman Filter, for extracting sinusoidal physiological signals, such as DPOAEs and ASSRs, from noise is described. The method includes signal modeling and fast signal processing algorithm. This method is also suitable for extracting any physiological signals of known frequency composition from background noise.

The method consists of the following steps. The signal is modeled. For enabling the use of the Kalman Filter for DPOAE signal processing, several models are developed for different processing tasks. These include models that are suitable for processing time-invariant frequency stimuli, models that are suitable for processing time-variant frequency stimuli, models that are suitable for processing the signal in which there is a strong power line interference (for example, 50 Hz, or 60 Hz interference), and models that suitable continuously setting a reference (or threshold) level for DPOAE, and also for other physiological signals.

The properties of the signal model are used for reducing the number of computational operations and therefore processing time. Variable step sizes are used, which leads to faster iteration, and shorter processing time. Re-initialization of the filter is avoided by introducing two parameters, which are referred to as a decay factor and a scale factor.

Several post-processing steps are also taken to maximize efficiency and ensure accuracy. Automatic reference (Thresholding) is used for preventing false detection (sound level display). A method for presenting estimation of DPOAEs as two-channel waveform output (audio output) is presented. A method for distinguishing ear-originated distortion product (DPOAE) from distortion product created by the recording system (calibration method) is also introduced.

"Biological" detection of physiological signals is also described. Physiological signals, such as DPOAEs, are extracted from noise and are presented to and detected by an operator. If the signal's frequency is not in the audible frequency and dynamic range, it is transposed into the audible frequency range and amplified so that an operator can comfortably hear it.

An embodiment of the invention will now be described in terms of DPOAE recording.

Figure 1:
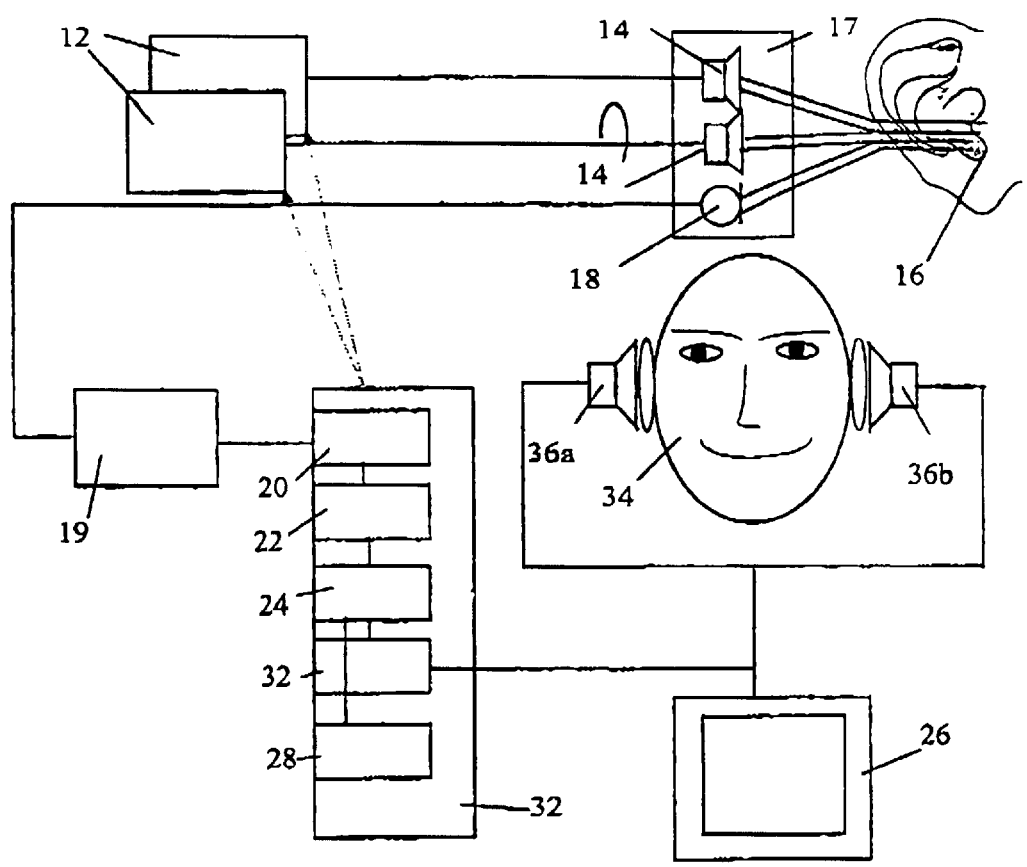
FIG. 1 is a block diagram of an ear testing system according to an embodiment of the invention

FIG. 1 shows a system for testing hearing according to the present embodiment of the invention, represented generally by the numeral 10. Two primary tones are generated electronically by computer controlled tone generators 12. The tones are presented by two speakers 14 into the occluded ear canal (the external auditory meatus) 16. Sounds in the ear canal 16 are recorded by a microphone 18 and transformed into electrical signals. The speakers 14 and microphone 18 are typical contained in a single device 17 for easy insertion into the ear. A low noise microphone pre-amplifier 19 amplifies the signal and an Analog-to-Digital (A/D) converter 20 transforms the electrical signal into its digital form. The digital signal is processed by a processor 22 for extracting the DPOAE both from the primaries and the noise. The DPOAE signal is analyzed by a processor 24, displayed by a display device (such as a monitor or the like) 26, and recorded on data storage (disk drive, CD-ROM, or the like) 28 in its digital form. These devices are typically contained in a computer 32. The processed DPOAE signal is transformed into its analog form by an Analog-to-Digital (A/D) converter 20 for analysis, display (visual or audio), and recording. An operator 34 wears a headset 36 with a pair of headphones 36a and 36b for listening to the analog signal.

The two primary tones have frequencies $f_1$ and $f_2$ ($f_1 < f_2$), and levels $L_1$ and $L_2$. Typically, the frequency $f_2$ is between 500 Hz and 10 kHz, the ratio $f_2/f_1$ is between 1.2 and 1.25, and the ratio $L_1/L_2$ is between minus 10 and plus 10 dB. The sounds recorded by the microphone 18 contain the two primary tones, physiological and background noise, and the Distortion Product Otoacoustic Emissions (if they are present). The strongest component of the sounds has the frequency $2f_{1-f2}$.

For digital signal processing, a linear mean-square error filter is used. The filter used is a Kalman Filter, which is a known approach to filtering, but it has not been previously used for the purpose of separation of DPOAEs from stimuli, and the extraction of the signals from noise.

The basics of the Kalman Filter are the following:
Given the following state model and observation model $$x[k+1]=G[k]x[k]+w[k] \quad (1)$$
$$z[k]=H[k]x[k]+v[k] \quad (2)$$

where
x[k] is m×1 state vector,
G[k] is m×m state matrix of constants, which is a description of the mth order difference equation model of the signal.
w[k] is m×1 vector sequence of Gausian white noise uncorrelated with both x[0] and v[k]
z[k] is n×1 observation vector
H[k] is n×m matrix of constants describing the relationship between the state vector and the observation vector.
v[k] is m×1 vector sequence of Gausian white noise uncorrelated with both x[0] and w[k]
x[0] m×1 initial state vector; a zero mean Gaussian random variable with convariance matrix P[0]
the covariance matrices of w and v are assumed to be known and have the form of $$E[w[j]w^T[k]] = Q[k] \quad j = k \quad (3)$$
$$= 0 \quad j \neq k$$

$$E[v[j]v^T[k]] = R[k] \quad j = k \quad (4)$$
$$= 0 \quad j \neq k$$

Figure 2:
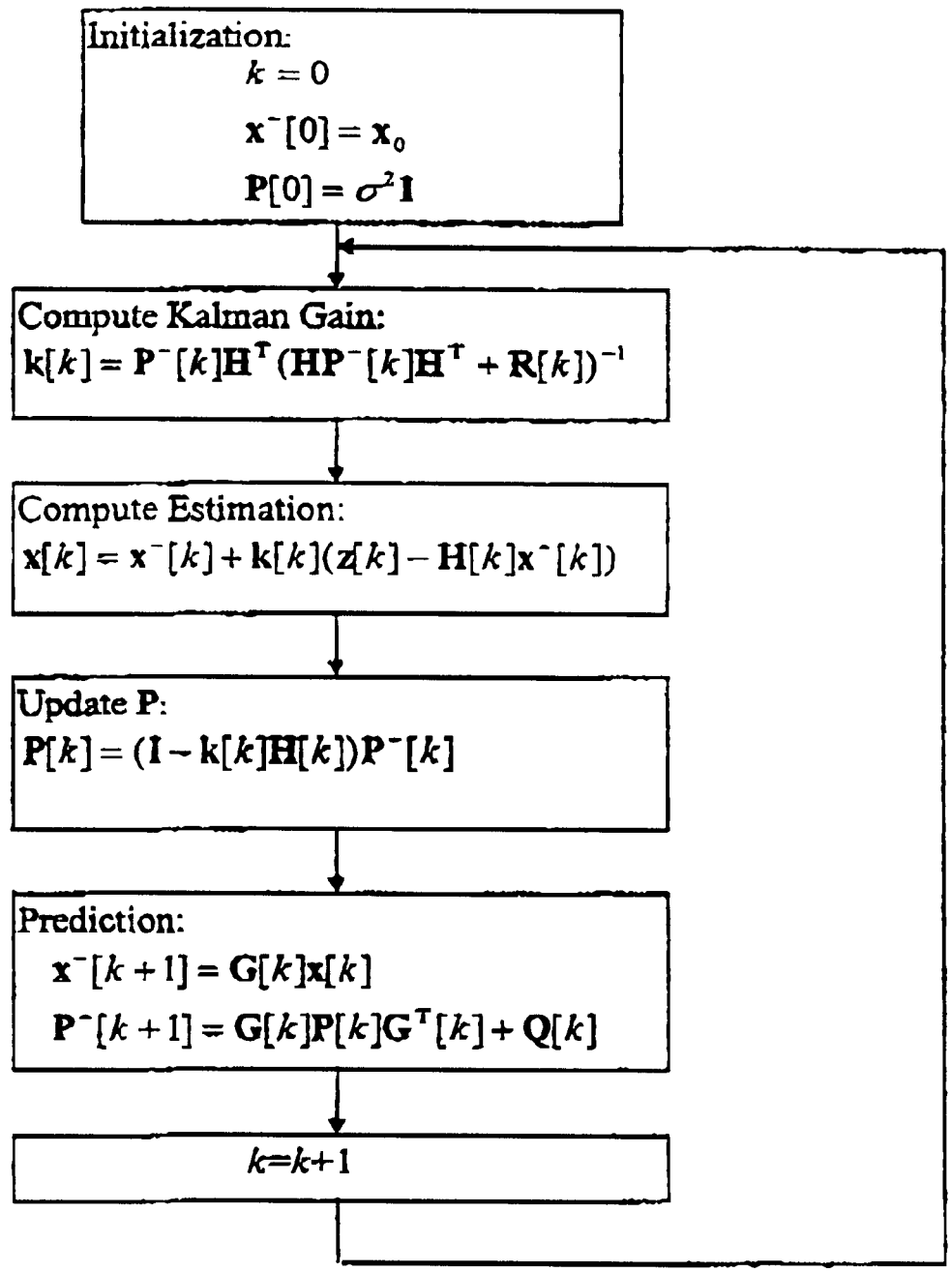
FIG. 2 is a flow diagram illustrating the operation of a Kalman filter.
Figure 3:
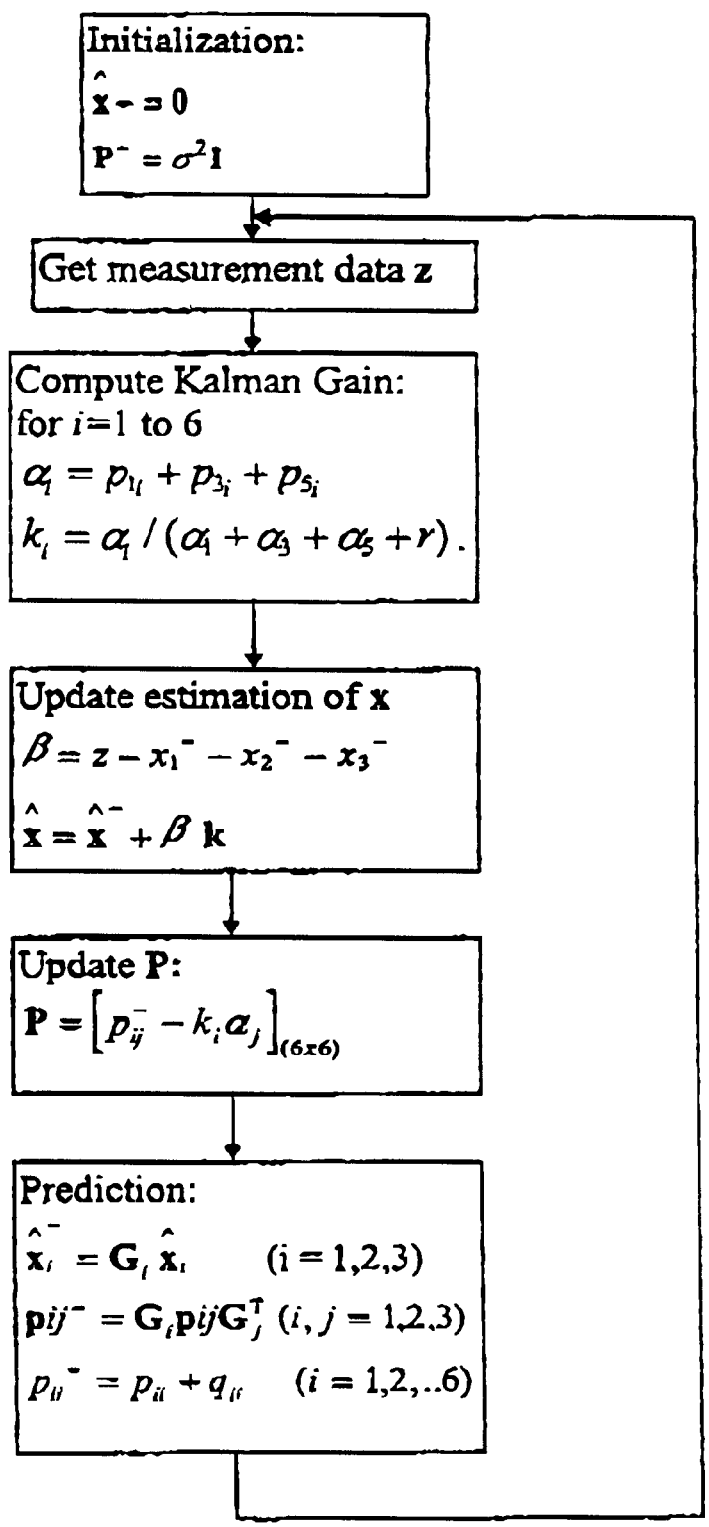
FIG. 3 is a flow diagram illustrating the operation of an improved Kalman filter for use with DPOAE detection.

FIG. 2 illustrates the algorithm for the Kalman Filter, which generates a Linear Minimum Mean Square Error Estimation of x.

The signal processing method is based on signal modeling. Below is provided an example for illustrating the details of the various modeling methods. If it is assumed that the measured signal consists of several major frequency elements (for example, indicated as $f_1, f_2, f_3, \ldots$), and these elements have different physical meanings, it is possible to obtain different models:

In the case of DPOAE testing, let $f_1, f_2, f_3$ be Primary One, Primary Two, and DPOAE respectively, and let z be the measured data from the, microphone and amplifier. Then obtain a model that can be used for processing the DPOAE signal (to be described below). In this model the state vector x has six elements, $x_0, x_1, x_2, x_3, x_4, x_5$, where $x_0$ and $x_1$ are related to f1; $x_2, x_3$ are related to $f_2$; $x_4$ and $x_5$ are related to $f_3$. In this model, $f_1, f_2$, and $f_3$ are time invariant. Thus the model is suitable for processing time-invariant frequency stimuli.

If $f_1, f_2, f_3, \ldots$ are frequencies that can be changed with time, the model becomes one that is suitable for time-variant frequency stimuli.

If one of $f_1, f_2, f_3, \ldots$ is equal to 60 (Hz) or 50 (Hz), then a model is obtained that is suitable for processing measured data which are contaminated by 60Hz (or 50 Hz) power line interference.

If $f_1, f_2$, and $f_3$ are the major elements in the measured data, $f_4$ can be a reference signal frequency which can be used to set a certain reference threshold. For example, in DPOAE testing, if the frequencies are set as $f_1$=Primary One frequency, $f_2$=Primary Two frequency, $f_3$=DPOAE frequency, and $f_4$=reference frequencies that are different from $f_3$, but very close to $f_3$ and slowly change with time, then $f_4$ can be used for continually setting the noise reference threshold for DPOAE measurement.

If $f_1$=frequency of ASSR, $f_2$=60(Hz), $f_3$=reference frequency a model that can be used to process the ASSR signal is obtained.

The following description details the DPAOE signal processing. The processing methods described below can be used directly in the above mentioned models.

(a) Signal Modeling:

$$x[k+1]=G[k]x[k]+w[k] \quad (1)$$
$$z[k]=Hx[k]+v[k] \quad (2)$$

$$G[k] = \begin{bmatrix} G_1 & 0 & 0 \\ 0 & G_2 & 0 \\ 0 & 0 & G_3 \end{bmatrix}$$

$$G_i = \begin{bmatrix} \cos(2\pi f_i/f_s) & -\sin(2\pi f_i/f_s) \\ \sin(2\pi f_i/f_s) & \cos(2\pi f_i/f_s) \end{bmatrix} (i=1,2,3)$$

$f_1, f_2$ are stimuli frequencies and $f_3$ is DPOAE frequency. $f_s$ is sampling frequency of the A/D converter $$H = [1 \ 0 \ 1 \ 0 \ 1 \ 0]$$

$$E\langle ww^T \rangle = \begin{bmatrix} Q_1 & 0 & 0 \\ 0 & Q_2 & 0 \\ 0 & 0 & Q_3 \end{bmatrix}$$

$$Q_i = \begin{bmatrix} q_i & 0 \\ 0 & q_i \end{bmatrix} (i=1,2,3, q_i \geq 0)$$

$$E\langle ww^T \rangle = r \ (r \geq 0)$$

$$x = \begin{bmatrix} x1 \\ x2 \\ x3 \end{bmatrix}$$

$$x_i = \begin{bmatrix} x_{2i-2} \\ x_{2i-1} \end{bmatrix} (i=1,2,3)$$

(b) Signal Processing Implementation:
denote Kalman Gain as $k=[k_i]_{(6 \times 1)}$
denote estimation error variance matrix as $P=[p_{ij}]_{(6 \times 6)}$
its block form is written as $$P = \begin{bmatrix} p_{11} & p_{12} & p_{13} \\ p_{21} & p_{22} & p_{23} \\ p_{31} & p_{32} & p_{33} \end{bmatrix}$$

The signal model has a special structure. Using the definition of the H matrix provided above, and the fact that P is a symmetric matrix, a substantial amount of multiplication in matrix computation can be avoided, thus increasing the processing speed. FIG. 2 illustrates an algorithm implementing this speed up.

The Kalman Filter by its nature is not an adaptive filter. When the real signal does not fit the model or when the filter has already gone into steady state. the filter output cannot reflect the real signal change. The filter must, therefore, be reinitiated otherwise the output stays in an incorrect state. This is a general problem when using Kalman Filters. The re-initialization method is not preferable in the present embodiment. This is because periodic re-initialization causes significant clicks. This problem is avoided by introducing an algorithm to control the model error.

Figure 4:
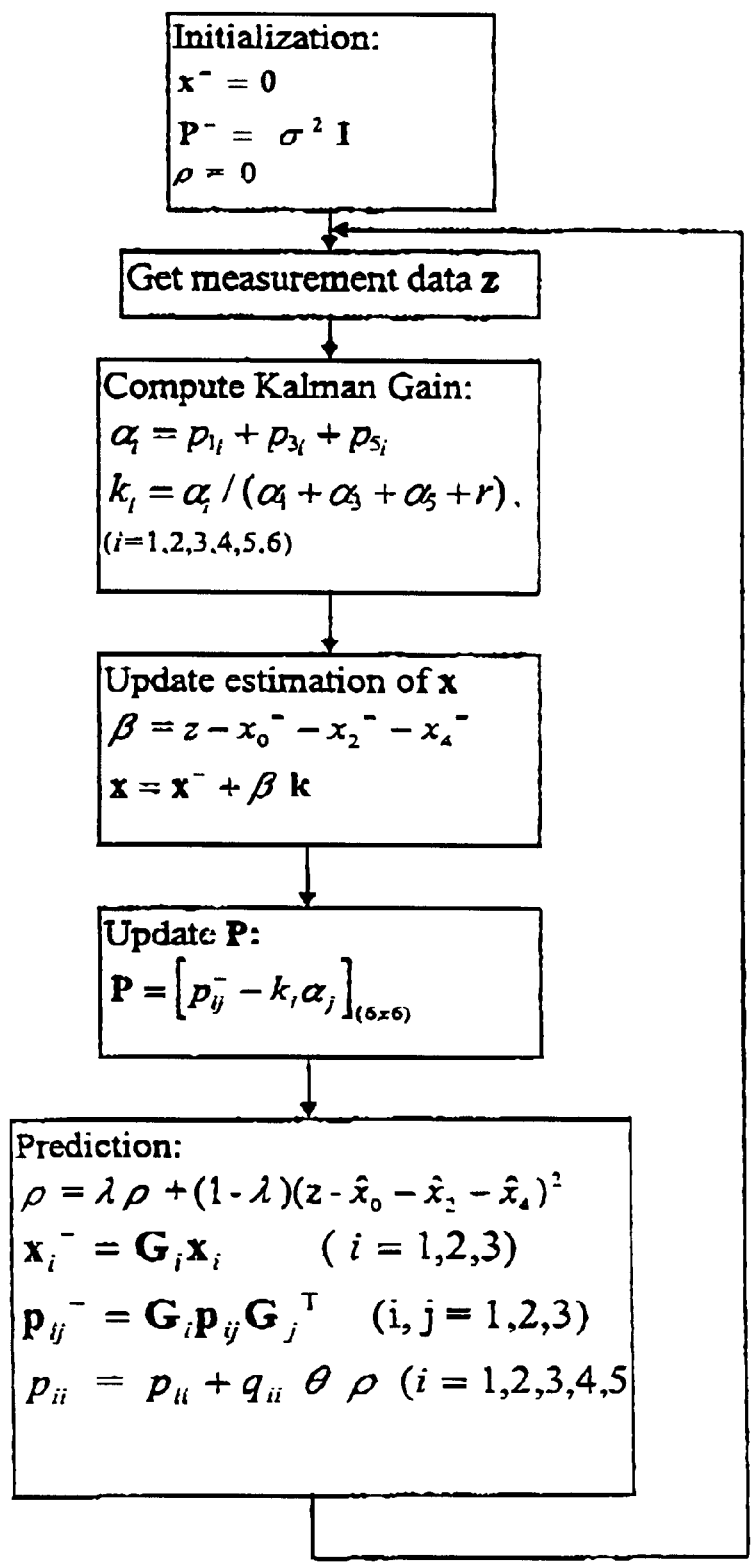
FIG. 4 is a flow diagram illustrating the operation of a further improved Kalman filter for use with DPOAE detection incorporating a decay factor and a scale factor.

Two parameters, herein referred to as a decay factor and a scale factor are, are defined. The decay factor is represented as $\lambda (0 \leq \lambda \leq 1)$, and the scale factor as $\theta (0 \leq \theta << 1)$. FIG. 4 illustrates the algorithm for a Kalman figure incorporating these factors. The values of $\lambda$ and $\theta$ modify the value of the error variance matrix, P. The factors are used together for widening the bandwidth of the filter. If fast testing speed is needed, the decay factor should be small. Similarly, if high accuracy is needed, the scale factor should be small. With this procedure the filter can track the sudden signal change without re-initialization, and keep accuracy at the same time.

In the algorithm shown in FIG. 4, the Kalman Gain and P matrix are updated in each iteration. The most time-consuming part of the computation in one iteration is updating the P matrix. It was noticed that after the loop started, the gain, K, gradually becomes steady. This characteristic is used to form an approximation algorithm. The fist step in the procedure is to calculate delta_K, where:

$$\text{delta\_}K = \|K(n) - K(n-1)\|.$$

If delta_K>t (where t is a threshold), then:

$$\text{Step} = [1 + \text{Step\_factor} * \|k(n-1)\| / \text{delta\_}K].$$

In this case, the filter may not update P and Gain in each iteration, only the estimation $\hat{x}$ is updated. After $\hat{x}$ is updated a number of times (or "Step" times), new gain, P and Step are computed. The threshold, t, is to prevent computation overflow. The Step_factor is to control speed. When high computation speed is required, a large Step_factor should be chosen. For high accuracy, a small Step_factor should be chosen.

Figure 5:
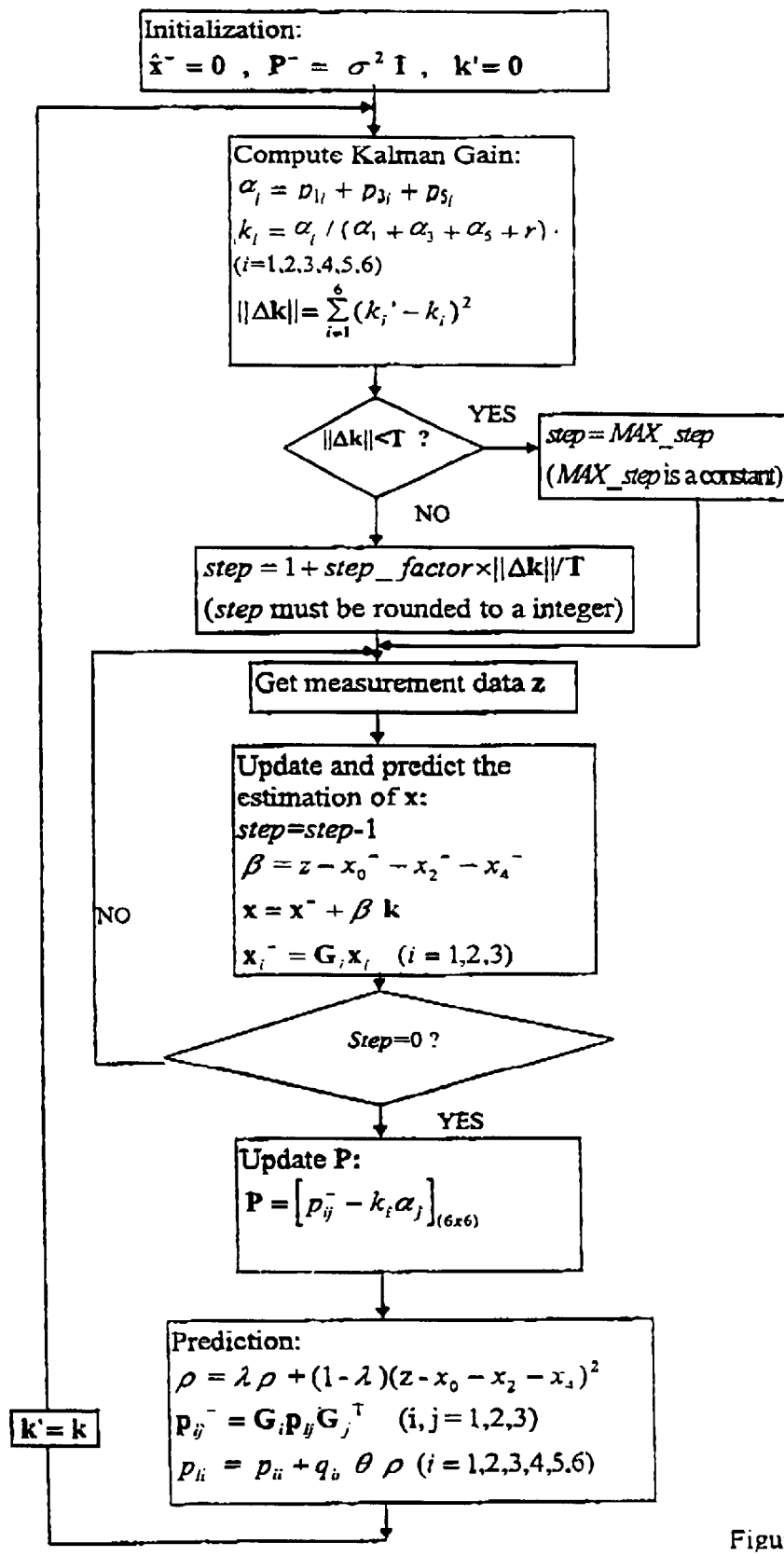
FIG. 5 is a flow diagram illustrating the operation of a ether improved Kalman filter for use with DPOAE detection incorporating a decay factor, a scale factor and a variable step.

If delta_K≤t, then Step=MAX_step (where MAX_step is the largest step size) and the speed is maximized. This procedure is particularly useful with slow computers. FIG. 5 illustrates the modifications to the previous algorithm for implementing his procedure.

The post-processing of a DPOAE signal has several coals. It is desirable to make the processed data more understandable for operators who may not be very familiar with the details of signal processing. Further, it is important to make the testing result more reliable (i.e. minimize false detection etc.). Finally, it is useful to transfer the Kalman Filter output to certain forms which operators can use for making their decisions easily.

All the useful information that the Kalman Filter can provide is contained in the estimation vector x. However, to the instrument operator, the information contained in x is not obvious. For the operator to use this information easily it is necessary to convert it to some form that is meaningful to the operators. The following are examples of some of the post-processing procedures.

One example is the use of an indicator for showing the level of primaries and DPOAEs. The levels are defined as:

Primary One ($f_1$) level:

$$L_1 = 10 \log(x_0^2 + x_1^2) / \text{ref\_amplitude}^2$$

Primary Two ($f_2$) level:

$$L_2 = 10 \log(x_2^2 + x_3^2) / \text{ref\_amplitude}^2$$

DPOAE ($f_3$) level:

$$L_3 = 10 \log(x_4^2 + x_5^2) / \text{ref\_amplitude}^2$$

Figure 6:
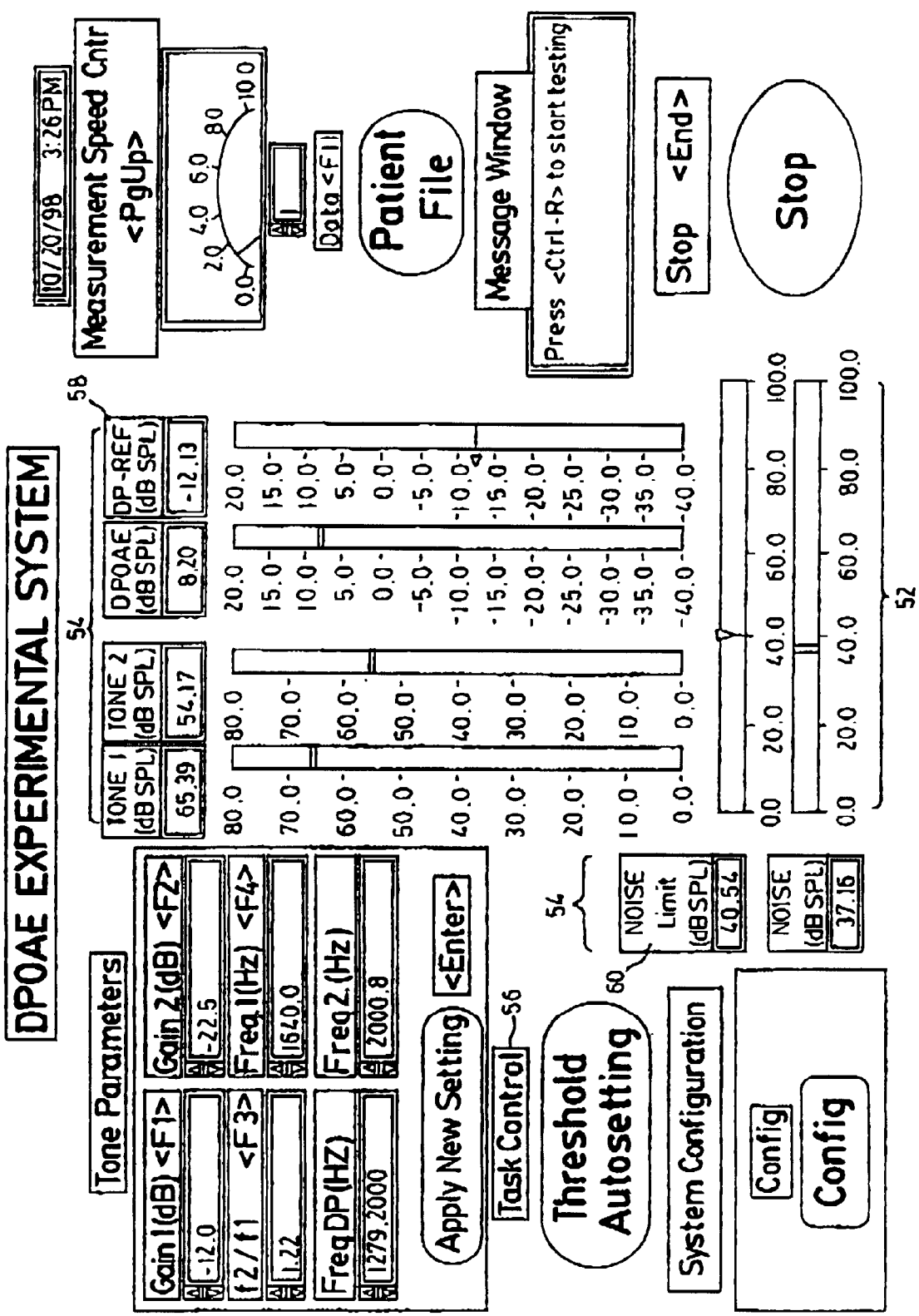
FIG. 6 is a block diagram of a sample output screen according to n embodiment of the invention.

Noise Level:

$$L_{noise} = 10 \log(z - x_0 - x_2 - x_4)^2 / \text{ref\_level}$$

where ref_amplitude is a value that correspond to 0 dB SPL. This value is determined by calibration FIG. 6 illustrates a sample output screen represented generally by the numeral 50. The screen 50 has both level bars 52 and numerical indicators 54 for displaying these levels.

Automatic reference (or thresholding) method can be used to limit or prevent false signal detection. The DPOAE level is denoted as $L_3$, the DPOAE threshold as L_DP_THR. the system DP-limit as L_DP_system. the measured noise level as L_noise, and the noise limit as L_noise_limit. Decisions regarding the origin of the detected signal are based on the following comparisons. If L_noise>L_noise_limit, or if $L_3$<L_DP_system, then a decision cannot be made regarding the origin of the signal (i.e., the DP is may originate not from the cochlea, but most likely from the recording system), and the result is not reliable.

If $L_3$>L_DP_system and L_noise<L_noise_limit, then a further comparison is required. That is, if L_>L_DP_THR, then it is confirmed that there is a DPOAE. If $L_3$<L_DP_THR then it is confirmed that there is no DPOAE.

There are two ways for setting L_DP_THR. The first is to separate the instrument operation session into two parts, which is shown in FIG. 6. By pressing the "task control button" <F9>56, the instrument can be switched between the "Normal Testing Mode" and the "Threshold Setting Mode". When the system works in the "Threshold Setting Mode", $f_3$ is set to frequencies that are close to but not equal to the DPOAE frequency, $2f_1-f_2$. The system performs measurements and updates the indicator of L_DP_THR 58 and L_noise_limit 60. When this indicator becomes stable then the operator can switch the system to work in the "Normal Testing Mode".

The second way for setting the L_DP_THR is by continually setting it. This is accomplished by adding a reference frequency component to the basic DPOAE model, as previously described. In this case, the operator does not need to switch the instrument to a different working mode and is, therefore, convenient for the operators. The associated cost is the extra computations required.

L_DP_system is a parameter that is related to the linearity of the overall system (from speaker to the microphone, amplifier and A/D converter). This parameter can be set by calibration, which is defined further on.

The DPOAE estimation is further presented as a two-channel audio output. Two signals are formed based on Kalman Filter estimation and output through a two-channel audio output. The Channel One signal is $$S_1:S1[k] = \text{output\_volume} \times \{x_4[k] + \alpha \times (z[k] - x_0[k] - x_2[k] - x_4[k])\}$$

And the Channel Two signal is $$S_2:S1[k] = \text{output\_volume} \times \{x_5[k] + \alpha \times (z[k] - x_0[k] - x_2[k] - x_4[k])\}$$

In the above equations, $(z[k]-x_0[k]-x_2[k]-x_4[k])$ is used as a reference signal. It is a wide-band signal. $\alpha(0<\alpha<1)$ is a parameter that controls the amplitude of the reference signal, It is preferred, but not required, that $\alpha$ is between 0.1 and 0.2.

The reason for adding a reference signal to output sound is that $x_4[k]$ is an optimal estimation of DPOAE, that is it has a high signal-to-noise ratio, and together with $x_5[k]$ it is used for obtaining an estimation of the intensity of the DPOAB. However, the human ear is more sensitive to frequency difference than intensity difference. Therefore, a wide band reference signal is added for making the composite signal much easier for the operator to listen to and detect whether or not there is a DPOAE signal present.

A calibration method is used in the decision-making procedure described above. In order to make the clinical testing reliable, the distortion caused by the recording system must be taken into account. The following is a sample procedure that can be used. Present two tones into a cavity (instead of the ear canal), and use the Kalman Filter algorithm to estimate the "signal" level at the frequency of the expected DPOAE, and store this level as L_DP_system. L_DP_system is a function of both intensities ($L_1$ and $L_2$) and frequencies ($f_1$ and $f_2$) of the two-tone stimulus, therefore an array of data obtained at different values of the stimulus intensities and frequencies should be used. This calibration can be done on-line or off-line.

The human ear has an extraordinary ability to detect sounds in presence of background noise. This is utilized in the detection of DPOAEs. The signal containing DPOAEs (if they are present), separated from the primaries and extracted from noise by the above described signal processing, is converted to analogue form and presented to an operator via loudspeakers or headphones. The operator can then detect DPOAEs with is or her own ears. This allows the operator to make fast analysis of whether or not DPOAEs are present in the ear tested.

Detection of signals, like DPOAEs, by an operator can simplify the testing procedure and device by eliminating read-outs, print-outs etc., and thus significantly decrease the cost of both testing and reporting its results. This is not possible with present-day methods.

Detection by a computer of DPOAEs is not preferred because there is always a distortion product present, which is produced by the recording system. It is difficult to distinguish between the two signals when the DPOAE level is at, or below, the level of the system's own distortion product. However, it is possible that a computer can do this analysis.

The method described provides several advantages. The signal processing method can generate a real time estimation of several parameters and waveforms at the same time. These include the level of the stimuli, the level of the response signal, the level of the noise, the waveform of stimuli, and the waveform of the response signal. Furthermore, no FFT is needed.

Since the primaries have already been removed from the DP waveform, no further filtering is needed. It can directly output from the signal processor, for example, to a speaker for an operator to listen to. In addition, all waveforms of the signal and stimuli (DPOAE, and the two primaries) consist of pairs of signals in quadrature (that is, 90 degree phase difference). This may be helpful for setting out criteria for screening purposes.

The system has the potential for being used in situations where the frequencies of stimuli are time variant. For that, all that is required is to form a G(k) that changes with time. The remainder of the algorithm remains the same. This not only allows the measurements of response signal at fixed frequencies of the stimuli, but also for a continual sweep of the stimuli over a frequency range, thus obtaining the frequency response of the signal as a monotonous function of the stimuli. Furthermore, the system has the potential for being used in situations where there is no stimulus signal at all. All that is required is a low SNR signal that can be modeled.

The algorithm can also be useful in other applications where a signal of known frequency composition must be detected with poor signal-to-noise ratios.

For example, in an alternate embodiment the system allows for continuous monitoring of signal levels in real time. Monitoring of signal levels may be useful during surgery. For example, monitoring the DPOAE levels during surgery on the auditory nerve, or in titrating ototoxic drugs, allows the operator to continuously monitor the physiological status of cochlea. For such a case, the output to the operator may not be in presented in a visual format. Rather, an alarm may be sounded when a predetermined threshold is surpassed. Once again, this approach is not limited to monitoring DPOAE level but may be extended to any other signal that would be useful to monitor, has a low SNR, and can be modeled.

Furthermore, since the system allows for continuous monitoring of the system in real time it may be used to calibrate devices such as hearing aids, pacemakers, eyeglasses and the like.

In a further embodiment, this method of signal processing can be used in immittance (impedance) audiometry (tympanometry and acoustic reflex measurements), where the middle ear is probed with a probe pure tone. The tone is typically of the frequency 226 Hz, in which the intensity of the tone can be reduced, without reduction of sensitivity, in order to reduce the patient's discomfort due to the probe tone. As well, the influence of acoustic artifacts can be reduced.

In yet a farther embodiment, the method of Signal processing can also be used in testing hearing aids, especially with low-level input signals, in order to decrease the influence of acoustic artifacts.

The method of signal processing and detection can also be used in recording and analyzing of many other physiological signals, for example, cardiac, visual, nervous and the like.

Physiological signals, such as DPOAEs and ASSRs, can be generalized as part of a class of signals that have known or expected frequencies, and are present in significant background noise. In order to detect such signals, it is necessary to perform signal processing. Although this description refers only to DPOAEs and ASSRs, it can easily be extended to the whole class of signals described above by a person skilled in the art. Furthermore, although the preferred embodiments refer only to use with a Kalmam filter a person skilled in the art could extend the application to include other filters.

The embodiments of the invention in which an exclusive property or privilege is claimed are defined as follows:

1. A signal processor for use in a real time system and for processing a signal with a low signal-to-noise ratio (SNR) comprising:
    a model for modeling an expected signal;
    a filter using said model for filtering said signal for generating a prediction of said signal and an error variance matrix; and
    an adaptive element for modifying said error variance matrix such that the bandwidth of said filter is widened;
    wherein said filter behaves like an adaptive filter.

2. A signal processor as defined in claim 1, wherein said filter is a Kalman filter 3. A signal processor as defined in claim 2, wherein said Kalman filter is digital.

4. A system for processing a signal with a low signal-to-noise ratio (SNR) for providing output to an operator comprising:
    a model for modeling an expected signal;
    a filter using said model for filtering said signal for generating a prediction of said signal and an error variance matrix; and
    an adaptive element for modifying said error variance matrix such that the bandwidth of said filter is widened;
    a processor for processing said filtered signal for determining signal characteristics of said signal;
    an output for providing said signal characteristics to said operator;
    wherein said system provides said output to said operator in real-time.

5. A system as defined in claim 4, wherein said filter is a Kalman filter.

6. A system as defined in claim 5, wherein said Kalman filter is digital.

7. A system as defined in claim 6, wherein said output is visually presented to said operator.

8. A system as defined in claim 7, wherein said visual output is displayed to said operator on monitor.

9. A system as defined in claim 6, further comprising a digital to analog converter for providing an analog signal to said operator, said analog signal dependent on said signal characteristics.

10. A system as defined in claim 9, wherein said analog signal is an audio output.

11. A system as defined in claim 10, wherein said analog signal is a direct representation of said signal.

12. A system as defined in claim 11, wherein the frequency of said audio output is adjusted such that it lies within the range of human hearing.

13. A system as defined in claim 11, wherein the amplitude of said audio output is increased.

14. A system as defined in claim 10, wherein said audio output is used for alerting said operator that said signal has passed a predetermined threshold.

15. A system as defined in claim 5, wherein said signal is a physiological signal.

16. A system as defined in claim 15, wherein said physiological signal is a distinguishing ear-originated distortion product (DPOAE).

17. A system as defined in claim 15, wherein said physiological signal is a auditory steady state response (ASSR).

18. A method for processing a signal with a low signal-to-noise ratio (SNR) for providing output to an operator comprising:
    modeling an expected signal;
    filtering said signal for generating a prediction of said signal and an error variance matrix;
    modifying said error variance matrix such that the bandwidth of said filter is widened;
    processing said filtered signal for determining signal characteristics;
    providing said signal characteristics to said operator;
    wherein said method provides said output to said operator in real-time.

19. A method as defined in claim 18 wherein said filtering is performed by a Kalman filter.

20. A method as defined in claim 19, wherein said Kalman filter is a digital filter.

21. A method as defined in claim 19, further comprising the steps of:
    converting said processed digital response signal to an analog format;
    providing said analog processed response signal to an operator.

22. A method as defined in claim 21, wherein said analog signal is an audio output.

23. A method as defined in claim 22, wherein said analog signal is a direct representation of said signal.

24. A method as defined in claim 23, wherein the frequency of said audio output is adjusted such that it lies within the range of human hearing.

25. A method as defined in claim 24, wherein the amplitude of said audio output is increased.

26. A method as defined in claim 22, wherein said audio output is used for alerting said operator that said signal has passed a predetermined threshold.

27. A method as defined in claim 19, wherein said signal is a physiological signal and is a distinguishable ear-originated distortion product (DPOAE).

28. A method as defined in claim 19, wherein said signal is a physiological signal and is a auditory steady state response (ASSR).

* * * * *